United States Patent
Plouhar et al.

(10) Patent No.: US 7,160,333 B2
(45) Date of Patent: *Jan. 9, 2007

(54) REINFORCED SMALL INTESTINAL SUBMUCOSA

(75) Inventors: Pamela L. Plouhar, South Bend, IN (US); Prasanna Malaviya, Ft. Wayne, IN (US); Joe W. Ferguson, Warsaw, IN (US); Mora C. Melican, Bridgewater, NJ (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 54 days.

This patent is subject to a terminal disclaimer.

(21) Appl. No.: 10/656,345

(22) Filed: Sep. 5, 2003

(65) Prior Publication Data

US 2004/0059431 A1 Mar. 25, 2004

Related U.S. Application Data

(63) Continuation of application No. 09/918,116, filed on Jul. 30, 2001, now Pat. No. 6,638,312.

(60) Provisional application No. 60/223,399, filed on Aug. 4, 2000.

(51) Int. Cl.
*A61F 2/02* (2006.01)

(52) U.S. Cl. .................................. 623/23.72

(58) Field of Classification Search .. 623/23.72–23.76, 623/23.61, 16.11; 606/151, 154

See application file for complete search history.

(56) References Cited

U.S. PATENT DOCUMENTS

| 3,272,204 | A |  | 9/1966 | Artandi et al. |
|---|---|---|---|---|
| 3,562,820 | A |  | 2/1971 | Braun |
| 4,352,463 | A |  | 10/1982 | Baker |
| 4,400,833 | A |  | 8/1983 | Kurland |
| 4,418,691 | A |  | 12/1983 | Yannas et al. |
| 4,610,397 | A |  | 9/1986 | Fischer et al. |
| 4,642,120 | A |  | 2/1987 | Nevo et al. |
| 4,703,108 | A |  | 10/1987 | Silver et al. |
| 4,873,976 | A |  | 10/1989 | Schreiber |
| 4,880,429 | A |  | 11/1989 | Stone |
| 4,902,508 | A |  | 2/1990 | Badylak et al. |
| 4,919,667 | A | * | 4/1990 | Richmond ............... 623/14.12 |
| 4,956,178 | A |  | 9/1990 | Badylak et al. |
| 4,956,179 | A |  | 9/1990 | Bamberg et al. |
| 5,007,934 | A |  | 4/1991 | Stone |
| 5,061,286 | A | * | 10/1991 | Lyle ........................ 623/23.63 |
| 5,102,421 | A |  | 4/1992 | Anspach, Jr. |
| 5,108,438 | A |  | 4/1992 | Stone |
| 5,128,326 | A |  | 7/1992 | Balazs et al. |
| 5,236,431 | A |  | 8/1993 | Gogolewski et al. |
| 5,246,441 | A |  | 9/1993 | Ross et al. |
| 5,275,826 | A |  | 1/1994 | Badylak et al. |

(Continued)

FOREIGN PATENT DOCUMENTS

EP 0 446 105 A2 1/1992

(Continued)

OTHER PUBLICATIONS

Hiles et al., "Mechanical properties of xenogeneic small-intestinal submucosa when used as an aortic graft in the dog", *Journal of Biomedical Materials Research*, vol. 29, 883-891, (1995).

(Continued)

*Primary Examiner*—Alvin J. Stewart
(74) *Attorney, Agent, or Firm*—Barnes & Thornburg LLP

(57) ABSTRACT

Bioprosthetic devices for soft tissue attachment, reinforcement, or construction are provided. The devices comprise a sheet of naturally occurring extracellular matrix and a sheet of synthetic mesh coupled to the naturally occurring extracellular matrix portion.

14 Claims, 3 Drawing Sheets

U.S. PATENT DOCUMENTS

| | | | |
|---|---|---|---|
| 5,281,422 A | 1/1994 | Badylak et al. | |
| 5,306,311 A * | 4/1994 | Stone et al. | 623/14.12 |
| 5,320,633 A | 6/1994 | Allen et al. | |
| 5,350,583 A * | 9/1994 | Yoshizato et al. | 623/15.12 |
| 5,352,463 A * | 10/1994 | Badylak et al. | 424/551 |
| 5,372,821 A | 12/1994 | Badylak et al. | |
| 5,374,268 A | 12/1994 | Sander | |
| 5,376,118 A | 12/1994 | Kaplan et al. | |
| 5,380,334 A | 1/1995 | Torrier et al. | |
| 5,445,833 A | 8/1995 | Badylak et al. | |
| 5,447,940 A | 9/1995 | Harvey et al. | |
| 5,460,962 A | 10/1995 | Kemp | |
| 5,479,033 A | 12/1995 | Baca et al. | |
| 5,514,181 A * | 5/1996 | Light et al. | 623/13.18 |
| 5,516,533 A | 5/1996 | Badylak et al. | |
| 5,554,389 A | 9/1996 | Badylak et al. | |
| 5,569,252 A | 10/1996 | Justin et al. | |
| 5,573,784 A | 11/1996 | Badylak et al. | |
| 5,591,234 A * | 1/1997 | Kirsch | 623/23.72 |
| 5,593,441 A * | 1/1997 | Lichtenstein et al. | 600/37 |
| 5,595,621 A | 1/1997 | Light et al. | |
| 5,601,558 A | 2/1997 | Torrie et al. | |
| 5,632,745 A | 5/1997 | Schwartz | |
| 5,641,518 A | 6/1997 | Badylak et al. | |
| 5,645,860 A | 7/1997 | Knapp, Jr. et al. | |
| 5,660,225 A * | 8/1997 | Saffran | 128/898 |
| 5,668,288 A | 9/1997 | Storey et al. | |
| 5,669,912 A | 9/1997 | Spetzler | |
| 5,677,355 A | 10/1997 | Shalaby et al. | |
| 5,681,353 A | 10/1997 | Li et al. | |
| 5,693,085 A * | 12/1997 | Buirge et al. | 623/1.13 |
| 5,695,998 A | 12/1997 | Badylak et al. | |
| 5,702,462 A | 12/1997 | Oberlander | |
| 5,711,969 A | 1/1998 | Patel et al. | |
| 5,730,933 A | 3/1998 | Peterson | |
| 5,733,337 A | 3/1998 | Carr, Jr. et al. | |
| 5,733,868 A | 3/1998 | Peterson et al. | |
| 5,735,897 A | 4/1998 | Buirge | |
| 5,735,903 A | 4/1998 | Li et al. | |
| 5,736,372 A | 4/1998 | Vacanti et al. | |
| 5,753,267 A | 5/1998 | Badylak et al. | |
| 5,755,791 A | 5/1998 | Whitson et al. | |
| 5,759,190 A | 6/1998 | Vibe-Hansen et al. | |
| 5,759,205 A | 6/1998 | Valentini | |
| 5,762,966 A | 6/1998 | Knapp et al. | |
| 5,769,899 A | 6/1998 | Schwartz et al. | |
| 5,773,577 A | 6/1998 | Cappello | |
| 5,788,625 A | 8/1998 | Plouhar et al. | |
| 5,795,353 A | 8/1998 | Felt | |
| 5,800,537 A | 9/1998 | Bell | |
| 5,830,708 A | 11/1998 | Naughton | |
| 5,834,232 A | 11/1998 | Bishop et al. | |
| 5,842,477 A | 12/1998 | Naughton et al. | |
| 5,847,012 A | 12/1998 | Shalaby et al. | |
| 5,855,613 A | 1/1999 | Antanavich et al. | |
| 5,855,619 A | 1/1999 | Caplan et al. | |
| 5,863,551 A | 1/1999 | Woerly | |
| 5,866,414 A | 2/1999 | Badylak et al. | |
| 5,885,619 A | 3/1999 | Patel et al. | |
| 5,899,939 A * | 5/1999 | Boyce et al. | 623/16.11 |
| 5,916,265 A | 6/1999 | Hu | |
| 5,922,028 A | 7/1999 | Plouhar et al. | |
| 5,939,323 A | 8/1999 | Valentini et al. | |
| 5,954,723 A | 9/1999 | Spetzler | |
| 5,954,747 A | 9/1999 | Clark | |
| 5,955,110 A | 9/1999 | Patel et al. | |
| 5,958,874 A | 9/1999 | Clark et al. | |
| 5,968,096 A | 10/1999 | Whitson et al. | |
| 5,971,987 A | 10/1999 | Huxel et al. | |
| 5,980,524 A | 11/1999 | Justin et al. | |
| 5,981,802 A | 11/1999 | Katz | |
| 5,981,825 A | 11/1999 | Brekke | |
| 5,989,269 A | 11/1999 | Vibe-Hansen et al. | |
| 5,989,280 A | 11/1999 | Euteneuer et al. | |
| 5,993,475 A | 11/1999 | Lin et al. | |
| 5,993,844 A | 11/1999 | Abraham et al. | |
| 5,997,575 A * | 12/1999 | Whitson et al. | 623/1.1 |
| 6,017,348 A | 1/2000 | Hart et al. | |
| 6,027,744 A * | 2/2000 | Vacanti et al. | 424/426 |
| 6,042,610 A | 3/2000 | Li et al. | |
| 6,051,750 A | 4/2000 | Bell | |
| 6,056,752 A | 5/2000 | Roger | |
| 6,056,777 A | 5/2000 | McDowell | |
| 6,056,778 A | 5/2000 | Grafton et al. | |
| 6,060,640 A * | 5/2000 | Pauley et al. | 623/23.72 |
| 6,068,648 A | 5/2000 | Cole et al. | |
| 6,077,989 A * | 6/2000 | Kandel et al. | 623/13.17 |
| 6,080,194 A | 6/2000 | Pachence et al. | |
| 6,093,201 A | 7/2000 | Cooper et al. | |
| 6,096,347 A | 8/2000 | Geddes et al. | |
| 6,099,567 A | 8/2000 | Badylak et al. | |
| 6,110,212 A | 8/2000 | Gregory | |
| 6,126,686 A | 10/2000 | Badylak et al. | |
| 6,146,385 A | 11/2000 | Torrie et al. | |
| 6,152,935 A | 11/2000 | Kammerer et al. | |
| 6,153,292 A | 11/2000 | Bell et al. | |
| 6,156,044 A | 12/2000 | Kammerer et al. | |
| 6,165,225 A * | 12/2000 | Antanavich et al. | 623/23.72 |
| 6,171,344 B1 | 1/2001 | Atala | |
| 6,176,880 B1 | 1/2001 | Plouchar et al. | |
| 6,179,840 B1 | 1/2001 | Bowman | |
| 6,179,872 B1 | 1/2001 | Bell et al. | |
| 6,187,039 B1 | 2/2001 | Hiles et al. | |
| 6,206,931 B1 | 3/2001 | Cook et al. | |
| 6,214,049 B1 * | 4/2001 | Gayer et al. | 623/16.11 |
| 6,224,892 B1 | 5/2001 | Searle | |
| 6,235,057 B1 | 5/2001 | Roger et al. | |
| 6,242,247 B1 | 6/2001 | Rieser et al. | |
| 6,251,143 B1 | 6/2001 | Schwartz et al. | |
| 6,251,876 B1 * | 6/2001 | Bellini et al. | 514/54 |
| 6,258,124 B1 | 7/2001 | Darois et al. | |
| 6,264,702 B1 * | 7/2001 | Ory et al. | 623/23.75 |
| 6,265,333 B1 * | 7/2001 | Dzenis et al. | 442/346 |
| 6,270,530 B1 | 8/2001 | Eldridge et al. | |
| 6,273,893 B1 | 8/2001 | McAllen, III et al. | |
| 6,280,473 B1 * | 8/2001 | Lemperle et al. | 623/16.11 |
| 6,283,980 B1 | 9/2001 | Vibe-Hansen et al. | |
| 6,288,043 B1 | 9/2001 | Spiro et al. | |
| 6,290,711 B1 | 9/2001 | Caspari et al. | |
| 6,293,961 B1 | 9/2001 | Schwartz et al. | |
| 6,294,041 B1 * | 9/2001 | Boyce et al. | 156/275.5 |
| 6,306,156 B1 | 10/2001 | Clark | |
| 6,306,159 B1 | 10/2001 | Schwartz et al. | |
| 6,306,177 B1 | 10/2001 | Felt et al. | |
| 6,319,258 B1 | 11/2001 | McAllen, III et al. | |
| 6,319,271 B1 | 11/2001 | Schwartz et al. | |
| 6,326,025 B1 | 12/2001 | Sigler et al. | |
| 6,333,029 B1 | 12/2001 | Vyakarnam et al. | |
| 6,334,872 B1 | 1/2002 | Termin et al. | |
| 6,355,699 B1 | 3/2002 | Vyakarnam et al. | |
| 6,358,284 B1 | 3/2002 | Fearnot et al. | |
| 6,364,884 B1 | 4/2002 | Bowman et al. | |
| 6,371,958 B1 | 4/2002 | Overaker | |
| 6,373,221 B1 | 4/2002 | Koike et al. | |
| 6,379,367 B1 | 4/2002 | Vibe-Hansen et al. | |
| 6,379,710 B1 | 4/2002 | Badylak | |
| 6,383,221 B1 | 5/2002 | Scarborough et al. | |
| 6,387,693 B1 * | 5/2002 | Rieser et al. | 435/297.1 |
| 6,409,764 B1 * | 6/2002 | White et al. | 623/16.11 |
| 6,440,444 B1 * | 8/2002 | Boyce et al. | 424/422 |
| 6,451,032 B1 | 9/2002 | Ory et al. | |
| 6,458,158 B1 * | 10/2002 | Anderson et al. | 623/16.11 |
| 6,458,383 B1 | 10/2002 | Chen et al. | |
| 6,464,729 B1 | 10/2002 | Kandel | |

| | | |
|---|---|---|
| 6,497,650 B1 | 12/2002 | Nicolo |
| 6,517,564 B1 | 2/2003 | Grafton et al. |
| 6,572,650 B1 | 6/2003 | Abraham et al. |
| 6,592,623 B1* | 7/2003 | Bowlin et al. ............ 623/14.13 |
| 6,638,312 B1* | 10/2003 | Plouhar et al. .......... 623/23.72 |
| 6,652,872 B1 | 11/2003 | Nevo et al. |
| 6,666,892 B1 | 12/2003 | Hiles et al. |
| 6,692,499 B1 | 2/2004 | Törmäläet al. |
| 6,812,221 B1 | 11/2004 | McKeehan et al. |
| 6,840,962 B1 | 1/2005 | Vacanti et al. |
| 2001/0024658 A1 | 9/2001 | Chen et al. |
| 2001/0043943 A1 | 11/2001 | Coffey |
| 2002/0019649 A1 | 2/2002 | Sikora et al. |
| 2002/0038151 A1* | 3/2002 | Plouhar et al. .......... 623/23.72 |
| 2002/0048595 A1 | 4/2002 | Geistlich et al. |
| 2002/0099448 A1 | 7/2002 | Hiles |
| 2002/0173806 A1 | 11/2002 | Giannetti et al. |
| 2003/0014126 A1 | 1/2003 | Patel et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0212447 A1 | 11/2003 | Euteneuer et al. |
| 2004/0143344 A1 | 7/2004 | Malaviya et al. |

FOREIGN PATENT DOCUMENTS

| | | |
|---|---|---|
| EP | 0 734 736 A1 | 10/1996 |
| GB | 2 215 209 | 9/1989 |
| JP | 11319068 A | 11/1999 |
| WO | WO 90/09769 | 9/1990 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | WO 96/24661 | 8/1996 |
| WO | WO 97/37613 | 10/1997 |
| WO | WO 98/06445 | 2/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 99/03979 | 1/1999 |
| WO | WO 99/43786 | 9/1999 |
| WO | WO 99/47188 | 9/1999 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 03/007788 A2 | 1/2003 |
| WO | WO 03/007790 A2 | 1/2003 |

OTHER PUBLICATIONS

Sandusky, et al., "Healing Comparison of Small Intestine Submucosa and ePTFE Grafts in the Canine Carotid Artery", *J. Surg.Res.*, 58:415-420, (1995).

Knapp, et al., "Biocompatibility of Small-Intestine Submucosa in Urinary Tract as Augmentation Cystoplasty Graft and Injectable Suspension", *J. Endourology*, 8:125-130, (1994).

Kropp et al., "Regenerative Bladder Augmentation: A Review of the Initial Preclinical Studies with Porcine Small Intestinal Submucosa", *Muscle, Matrix, and Bladder Function*, Plenum Press, New York, (1995).

Kropp et al., "Experimental Assessment of Small Intestinal Submucosa as a Bladder Wall Substitute", *Urology* 446:396-400, (1995).

Vaught et al., "Detrusor Regeneration in the Rat Using Porcine Small Intestinal Submucosa Grafts: Functional Innervation and Receptor Expression", *J. Urol.*, 155:374-378, (1996).

Kropp et al, Characterization of Small Intestinal Submucosa Regenerated Canine Detrusor: Assessment of Reinnervation, In Vitro Compliance and contractility, *J. of Urol*, 156:599-607, (1996).

Kropp et al., "Regenerative Urinary Bladder Augmentation Using Small Intestinal Submucosa: Urodynamic and Histopathologic Assessment in Long-Term Canine Bladder Augmentations", *Journal of Urology*, 155:2098-2104, (1996).

Aiken et al., "Small Intestinal Submucosa as an Intra-Articular Ligamentous Graft Material: A Pilot Study in Dogs", *Vet Comp Orthopedics Traumatology*, 7:124-128, (1994).

Badylak et al., "The Use of Xenogeneic Small Intestinal Submucosa as a Biomaterial for Achille's Tendon Repair in a dog model", *J Biomed Materials*, 29:977-985, (1995).

Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).

Ferrand et al., "Directional Porosity of Porcine Small-Intestinal Submucosa", *J Biomed Materials Res*, 27:1235-1241, (1993).

Hiles et al., "Porosity of Porcine Small-Intestinal Submucosa for use as a Vascular Graft", *J Biomed Materials Res*, 27:139-144, (1993).

Hodde et al., "Glycosaminoglycan Content of Small Intestinal Submucosa: A Bioscaffold for Tissue Replacement", *Tissue Engineering*, 2:3, 209-217, (1996).

Prevel et al., "Small Intestinal Submucosa: Utilization for Repair of Rodent Abdominal Wall Defects", *Ann Plast Surg*, 35:374-380, (1995).

Clarke et al., "Intestine Submucosa and Polypropylene Mesh for Abdominal Wall Repair in Dogs", *J Surg Res*, 60:107-114, (1996).

Prevel et al., "Small Intestinal Submucosa: Utilization as a Wound Dressing in Full-Thickness Rodent Wounds", *Ann Plast Surg.* 35:381-388, (1995).

Cobb et al., "Histology after Dural Grafting with Small Intestinal Submucosa", *Surgical Neurology*, 46:389-394, (1996).

Cobb et al., "Porcine Small Intestinal Submucosa as a Dural Substitute", *Surgical Neurology*, 51:99-104, (1999).

Voytik-Harbin et al., "Application and Evaluation of the AlamarBlue Assay for Cell Growth and Survival of Fibroblasts", *Journal of Immunological Methods, In Vitro Cell Bio-Animal*, 34:2399-246, (1998).

Suckow, M.A., "Enhanced Bone Regeneration Using Porcine Small Intestinal Sumucosa", *J. Invest Surg*, 12:277, (1999).

Badylak, S., et al., "Naturally Occurring Extracellular Matrix as a Scaffold for Musculoskeletal Repair", *Clin Orthop*, 3675:S333-S3433, (1999).

Cook, J.L. et al., "Induction of Meniscal Regeneration in Dogs Using a Novel Biomaterial", *Am J Sports Med*, 27:658, (1999).

Dejardin, L.M. et al., "Use of small intestinal submucosal implants for regeneration of large fascial defects: an experimental study in dogs", J Biomed Mater Res, 46:203-211, (1999).

Sacks, M.S., et al., "Quantification of the fiber architecture and biaxial mechanical behavior of porcine intestinal submucosa", *J Biomed Mater Res*, 46:1-10, (1999).

COOK® News Releases, "COOK® Introduces Innovative Surgisis™ Soft Tissue Repair Biomaterial", (May 21, 2000).

COOK® News Releases, "COOK® Oasis™ Wound Dressing Biomaterial From COOK® Remodels Partial Thickness Skin Injuries", (Dec. 23, 1999).

COOK® News Releases, "Cook Incorporated Forms Dedicated Tissue Engineered Products Group", (Feb. 16, 2000).

COOK® News Releases, "FDA Clears Oasis™ Wound Dressing Biomaterial From COOK® For Full-Thickness Skin Injuries", (Jan. 24, 2000).

Lenz, et al., "SIS as an ACL Replacement in Dogs and Goats," First Symposium, Dec. 1996, USA.

Cook, et al., "Comparison of SIS Cancellous Bone as Substrates for Three-Dimensional Culture of Canine Articular Chondrocytes," First SIS Symposium, Dec. 1996, USA.

Badylak, et al., "Different Configurations of Small Intestinal Submucosa as a Biomaterial for Achilles Tendon Repair in a Dog Model," First SIS Symposium, Dec. 1996, USA.

Voytik-Harbin & Badylak, "Induction of Osteogenic Activity By Small Intestinal Submucosa in Rat Calvaria Non-union Defects," First SIS Symposium, Dec. 1996, USA.

Kandel, et al., "SIS and Reconstituted Cartilage and Its Use in Joint Resurfacing of Focal Defects in Rabbits," First SIS Symposium, Dec. 1996, USA.

Tullius, et al., "Differential Permeabilty of SIS," First SIS Symposium, Dec. 1996, USA.

Obermiller, et al., "Suture Retention Strength of SIS," First SIS Symposium, Dec. 1996, USA.

Shelton, et al., "Repair of the Canine Medial Meniscus using SIS: A Feasibility Study," Second SIS Symposium, Dec. 1998, USA.

Cook, et al., "Meniscal Regeneration in dogs Using Grafts of SIS," Second SIS Symposium, Dec. 1998, USA.

Welch, et al., "Healing of Canine Meniscal Defect with Small Intestinal Submucosa Implants," Dec. 1998, USA.

Solchaga, et al., "SIS as Delivery Vehicle for Mesenchymal Progenitor Cells," Dec. 1998, USA.

Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates The Differentiation of Myofibroblasts," Third SIS Symposium, Nov. 2000, USA.

Cook, et al., "Tissue Engineering For Meniscal Repair Using SIS," Third SIS Symposium, Nov. 2000, USA.

Lifrak, et al., "Enhanced Repair of Goat Meniscal Defects Using Porcine Small Intestinal Submucosa (SIS)," Third SIS Symposium, Nov. 2000, USA.

Hoffman, "SIS Disc Replacement For the Temporomandibular Joint," Third SIS Symposium, Nov. 2000, USA.

Kaeding, "Use of SIS in The Surgical Treatment of Chronic Symptomatic Patella Tendinosis," Third SIS Symposium, Nov. 2000, USA.

Tomczak and Kaeding, "Use of SIS in The Surgical Treatment of Tendinosis About The Foot And Ankle," Third SIS Symposium, Nov. 2000, USA.

Moore, et al., "Bridging Segmental Defects In Long Bones With Intramedullary Tubes And Periosteal Sleeves Made From Small Intestinal Submucosa (SIS)," Third SIS Symposium, Nov. 2000, USA.

Wang, et al., "Small Intestinal Submucosa Enhances Healing of Medical Collateral Ligament In A Rabbit Model," Third SIS Symposium, Nov. 2000, USA.

Ojha, et al., "PGA-Plla Versus Small Intestinal Submucosa (SIS): A Comparison of Neo-Cartilage Grown From Two Scaffold Materials," Third SIS Symposium, Nov. 2000, USA.

Wiklerson, "Use of The Porcine Small Intestine Submucosal Tissue Graft And Repair of Rotator Cuff Tears," Third SIS Symposium, Nov. 2000, USA.

"Small Intestinal Submucosa," Third SIS Symposium, Nov. 2000, USA.

"Current Clinical Applications of SIS," Third SIS Symposium, Nov. 2000, USA.

Hodde, et al., "Glycosaminoglycan Content of Small Intestinal Submucosa: A Potential for GAG-Growth Interactions In SIS-Mediated Healing", First Symposium, Dec. 1996, USA.

Definitions of "intertwine" and "twine", *American Heritage Dictionary of the English Language Online*, Accessed Sep. 29, 2005, 2 pgs.

How to Cut Meat Products 2001, *Urschel Corp.*, Accessed online at fr.urschel.com/literature/HTCMeat.pdf on Oct. 3, 2005, 8 pgs.

Definitions of "comminute" and "slurry", *Dictionary.com*; Accessed Sep. 20, 2005, 2 pgs.

Friess, "Collagen in drug delivery and tissue engineering", *Advanced Drug Delivery Reviews*, vol. 55, No. 12, 2003, pp. 1529-1530.

Olsen et al., "Recombinant collagen and gelatin for drug delivery", *Advanced Drug Delivery Reviews*, vol. 55, No. 12, 2003, pp. 1547-1567.

Aigner et al., "Collagens-major component of the physiological cartilage matrix, major target of cartilage degeneration, major tool in cartilage repair", *Advanced Drug Delivery Reviews*, vol. 55, No. 12, 2003, pp. 1569-1593.

Geiger et al., "Collagen sponges for bone regeneration with rhBMP-2", *Advanced Drug Delivery Reviews*, vol. 55, No. 12, 2003, pp. 1613-1629.

Ruszczak et al., "Collagen as a carrier for on-site delivery of antibacterial drugs", *Advanced Drug Delivery Reviews*, vol. 55, No. 12, 2003, pp. 1679-1698.

O'Grady et al., "Global regulatory registration requirements for collagen-based combination products: points to consider", *Advanced Drug Delivery Reviews*, vol. 55, No. 12, 2003, pp. 1699-1721.

Matthews et al., "Electrospinning of Collagen Type II: A Feasibility Study", *Journal of Bioactive and Compatible Polymers*, vol. 18, Mar. 2003, pp. 125-134.

Biscarini et al., "Growth of High Vacuum Sublimed Oligomer Thin Films", *ACS Polymer Preprints*, vol. 37, No. 2, 1996, pp. 618-619.

Biscarini et al., "Morphology and roughness of high-vacuum sublimed oligomer thin films", *Thin Solid Films*, vol. 439-443, 1996, pp. 284-285.

Biscarini et al., "Scaling Behavior of Anisotropic Organic Thin Films Grown in High-Vacuum", *Physical Review Letters*, vol. 78, No. 12, Mar. 24, 1997, pp. 2389-2392.

Voytik-Harbin et al., "Identification of Extractable Growth Factors from Small Intestinal Submucosa", *Journal of Cellular Biochemistry*, vol. 67, 1997, pp. 478-491.

McPherson, Ph.D. et al., "Characterization of Fibronectin Derived from Porcine Small Intestinal Submucosa", *Tissue Engineering*, vol. 4, No. 1, 1998, pp. 75-83.

Hodde, et al., "Vascular Endothelial Growth Factor in Porcine-Derived Extracellular Matrix", *Endothelium*, vol. 8(1), 2001, pp. 11-24.

Hodde et al., "Wounds: A Compendium of Clinical Research and Practice", *Website:* http:www.hmpcommunications.com/WNDS, Printed: Jul. 12, 2005, 7 pgs.

Hurst et al., "Mapping of the distribution of significant proteins and proteoglycans in small intestinal submucosa by fluorescence microscopy", *J. Biomater. Sci. Polymer Edn.*, vol. 12, No. 11, 2001, pp. 1267-1279.

Hodde et al., "Fibronectin peptides mediate HMEC adhesion to porcine-derived extracellular matrix", *Biomaterials*, vol. 23, 2002, pp. 1841-1848.

Hodde, "Naturally Occurring Scaffolds for Soft Tissue Repair and Regeneration", *Tissue Engineering*, vol. 8, No. 2, 2002, pp. 295-308.

Allman et al., Xenogeneic Extracellular Matrix Grafts Elicit a Th2-Restricted Immune Response, *Transplantation*, vol. 71, No. 11, Jun. 15, 2001, pp. 1631-1640.

Allman et al., "The Th2-Restricted Immune Response to Xenogeneic Small Intestinal Submucosa Does Not Influence Systemic Protective Immunity to Viral and Bacterial Pathogens", *Tissue Engineering*, vol. 8, No. 1, 2002, pp. 53-62.

Krcma, "Nonwoven Textiles", *Textile Trade Press*, Manchester, England, 1962, 6 pgs.

Answers.com,. Definition of "freeze-dry", Accessed on May 12, 2005, 6 pgs.

Ma et al., "Microtubular architecture of biodegradable polymer scaffolds", *J. Biomed Materials Res.*, vol. 56, No. 4, 2001, pp. 469-477.

Ma et al., "Biodegradable Polymer Scaffolds with Well-Defined Interconnected Spherical Pore Network", *Tissue Engineering*, vol. 7, No. 1, 2001, pp. 23-33.

Klawitter et al., "An Evaluation of Bone Growth into Porous High Density Polyethylene", *J. Biomed. Materials Res.*, vol. 10, (1976) pp. 311-323.

White et al., "Biomaterial Aspects of Interpore-200 Porous Hydroxyapatite", *Dental Clinics of North America*, Reconstructive Implant Surgery and Implant Prosthodontics 1, vol. 30, No. 1, pp. 49-67.

Shors, Coralline Bone Graft Substitutes, *Orthopaedic Clinics of North America*, Bone Grafting and Bone Graft Substitutes, vol. 30, No. 4, Oct. 1999, pp. 599-613.

Wang, Experimental Study of Osteogenic Activity of Sintered Hydroxyapatite—On the Relationship of Sintering Temperature and Pore Size—, *J. Jpn. Orthop. Assoc.*, vol. 64, 1990, pp. 847-859.

Nehrer et al., "Matrix collagen type and pore size influence behavior of seeded canine chondrocytes", *Biomaterials*, vol. 18, No. 11, 1997, pp. 769-776.

Salem et al., "Interactions of 3T3 fibroblasts and endothelial with defined pore ffeatures", *J. Biomed Materials Res.*, vol. 61, No. 2, 2002, pp. 212-217.

Klootwyk, et al., "The Use of Xenographic SIS as a Biomaterial for Achilles Tendon Repair in Dogs," *First SIS Symposium*, Dec. 1996, USA.

\* cited by examiner

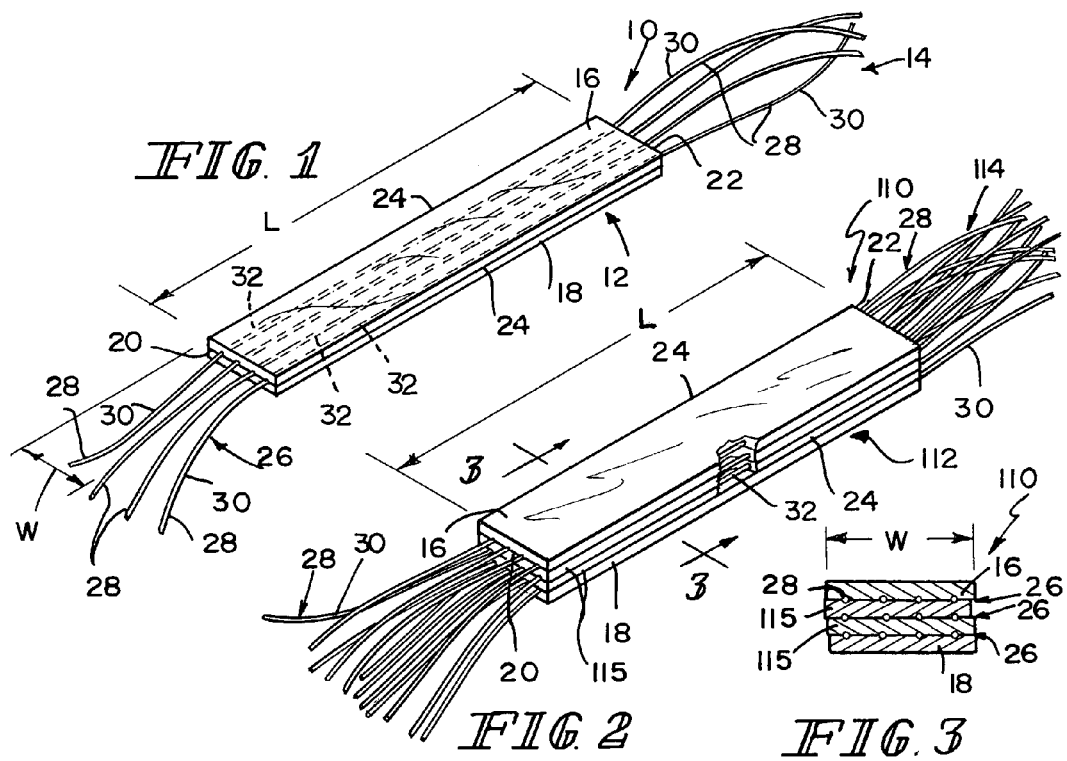
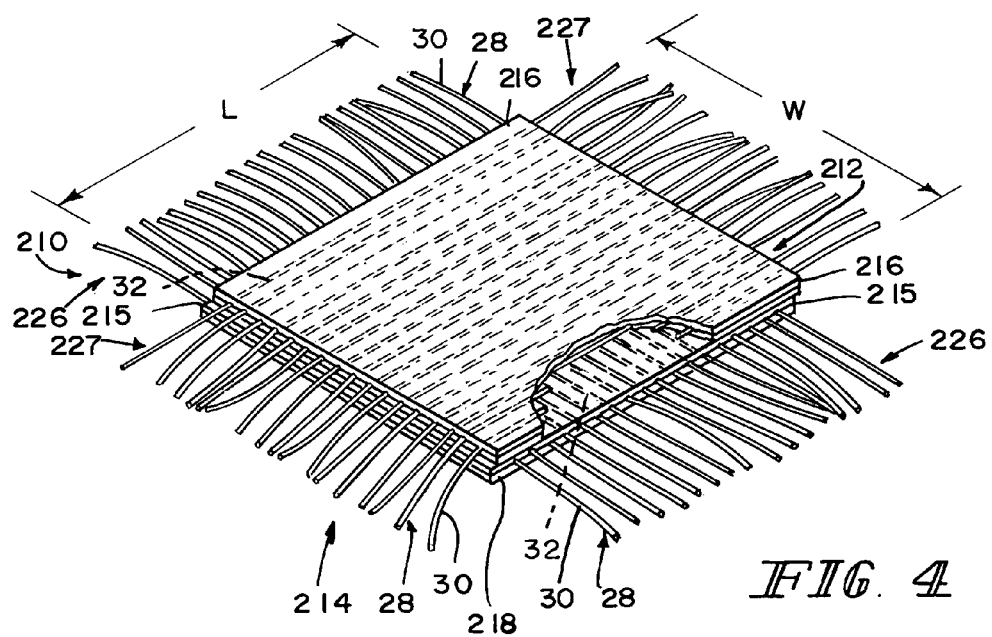

REINFORCED SMALL INTESTINAL SUBMUCOSA

This application is a continuation of U.S. patent application Ser. No. 09/918,116, filed Jul. 30, 2001, now U.S. Pat. No. 6,638,312, which claims priority under 35 U.S.C. 119(e) to U.S. Provisional Application Ser. No. 60/223,399, filed Aug. 4, 2000, which is expressly incorporated by reference herein.

FIELD OF THE INVENTION

The present invention relates to bioprosthetics and particularly to the use of bioprosthetics for the repair and replacement of connective tissue. More particularly, the present invention relates to the use of a composite bioprosthetic device made up of a synthetic portion and heterologous animal tissue.

BACKGROUND AND SUMMARY OF THE INVENTION

Currently there are multiple patents and publications that describe in detail the characteristics and properties of small intestine submucosa (SIS). See, for example, U.S. Pat. Nos. 5,352,463, 4,902,508, 4,956,178, 5,281,422, 5,372,821, 5,445,833, 5,516,533, 5,573,784, 5,641,518, 5,645,860, 5,668,288, 5,695,998, 5,711,969, 5,730,933, 5,733,868, 5,753,267, 5,755,791, 5,762,966, 5,788,625, 5,866,414, 5,885,619, 5,922,028, 6,056,777, and WO 97/37613, incorporated herein by reference. SIS, in various forms, is commercially available from Cook Biotech Incorporated (Bloomington, Ind.). Further, U.S. Pat. No. 4,400,833 to Kurland and PCT publication having International Publication Number WO 00/16822 provide information related to bioprosthetics and are also incorporated herein by reference.

There are currently many ways in which various types of soft tissues such as ligaments or tendons, for example, are reinforced and/or reconstructed. Suturing the torn or ruptured ends of the tissue is one method of attempting to restore function to the injured tissue. Sutures may also be reinforced through the use of synthetic non-bioabsorbable or bioabsorbable materials. Autografting, where tissue is taken from another site on the patient's body, is another means of soft tissue reconstruction. Yet another means of repair or reconstruction can be achieved through allografting, where tissue from a donor of the same species is used. Still another means of repair or reconstruction of soft tissue is through xenografting in which tissue from a donor of a different species is used.

According to the present invention, a bioprosthetic device for soft tissue attachment, reinforcement, and/or reconstruction is provided. The bioprosthetic device comprises a small intestinal submucosa (SIS) or other naturally occurring extracellular matrix (ECM), formed to include a tissue layer of SIS, and a synthetic portion coupled to the SIS tissue layer. The tissue layer of SIS may also be dehydrated.

In preferred embodiments, the SIS portion of the bioprosthetic device includes a top tissue layer of SIS material and a bottom tissue layer of SIS material coupled to the top tissue layer. The synthetic portion of the bioprosthetic device includes a row of fibers positioned to lie between the top and bottom tissue layers of the SIS portion. The fibers are positioned to lie in a spaced-apart coplanar relation to one another along a length, L, of the SIS portion. The fibers are each formed to include a length L2, where L2 is longer than L so that an outer end portion of each fiber extends beyond the SIS portion in order to anchor the bioprosthetic device to the surrounding soft tissue.

In other embodiments, the synthetic portion of the bioprosthetic device includes a mesh member formed to define the same length, L, as the SIS portion. In yet another embodiment, the synthetic portion of the bioprosthetic device includes a mesh member having a body portion coupled to the SIS portion and outer wing members coupled to the body portion and positioned to extend beyond the length, L, and a width, W, of the SIS portion in order to provide more material for anchoring the bioprosthetic device to the surrounding soft tissue.

SIS is intended to identify small intestine submucosa. While porcine SIS is widely used, it will be appreciated that small intestine submucosa may be obtained from other animal sources, including cattle, sheep, and other warm-blooded mammals. Further, other sources of extracellular matrices from various tissues are known to be effective for tissue remodeling as well. These sources include, but are not limited to, stomach, bladder, alimentary, respiratory, and genital submucosa. See, e.g., U.S. Pat. Nos. 6,171,344, 6,099,567, and 5,554,389, hereby incorporated by reference. Such submucosa-derived matrices comprise highly conserved collagens, glycoproteins, proteoglycans, and glycosaminoglycans. Additionally, other ECMs are known, for example lamina propria and stratum compactum.

For the purposes of this invention, it is within the definition of a naturally occurring ECM to clean, delaminate, and/or comminute the ECM, or even to cross-link the collagen fibers within the ECM. However, it is not within the definition of a naturally occurring ECM to extract and purify the natural fibers and refabricate a matrix material from purified natural fibers. Compare WO 00/16822 A1. Thus, while reference is made to SIS, it is understood that other naturally occurring ECMs are within the scope of this invention.

Fiber is intended to identify a synthetic reinforcement component present within the implant to contribute enhanced mechanical and handling properties. The reinforcement component is preferably in the form of a braided suture or a mesh fabric that is biocompatible. The reinforcement component may be bioabsorbable as well.

The reinforcing component of the tissue implant of the present invention may be comprised of any absorbable or non-absorbable biocompatible material, including textiles with woven, knitted, warped knitted (i.e., lace-like), non-woven, and braided structures. In an exemplary embodiment the reinforcing component has a mesh-like structure. In any of the above structures, mechanical properties of the material can be altered by changing the density or texture of the material. The fibers used to make the reinforcing component can be, for example, monofilaments, yarns, threads, braids, or bundles of fibers. These fibers can be made of any biocompatible material, including bioabsorbable materials such as polylactic acid (PLA), polyglycolic acid (PGA), polycaprolactone (PCL), polydioxanone (PDO), trimethylene carbonate (TMC), polyvinyl alcohol (PVA), and copolymers or blends thereof. In an exemplary embodiment, the fibers that comprise the mesh are formed of a polylactic acid and polyglycolic acid copolymer at a 95:5 mole ratio.

Additional features of the present invention will become apparent to those skilled in the art upon consideration of the following description of preferred embodiments of the invention exemplifying the best mode of carrying out the invention as presently perceived.

BRIEF DESCRIPTION OF THE DRAWINGS

The detailed description particularly refers to the accompanying figures in which:

FIG. 1 is a perspective view showing a composite bioprosthetic device of the present invention formed to include a small intestinal submucosa (SIS) portion and a synthetic portion and showing the SIS portion including a top tissue layer of SIS material and a bottom tissue layer of SIS material and further showing the synthetic portion including a row of four fibers positioned to lie in coplanar relation to each other between the top and bottom tissue layers of the SIS portion and positioned to run longitudinally along a length of the SIS portion and extend beyond a first and second end of the SIS portion in order to anchor the bioprosthetic device to surrounding soft tissue;

FIG. 2 is a perspective view similar to FIG. 1 showing an SIS portion of another bioprosthetic device of the present invention being formed to include a top layer, a bottom layer, and two middle layers positioned to lie between the top and the bottom layers and a synthetic device being formed to include three rows of four fibers so that each row is positioned to lie between each of the adjacent tissue layers of the SIS portion so that each fiber is positioned to run longitudinally along a length, L, of the SIS portion;

FIG. 3 is a sectional view taken along line 3—3 of FIG. 2 showing the top, bottom, and middle tissue layers of the SIS portion and also showing the three rows of fibers of the synthetic portion of the bioprosthetic device;

FIG. 4 is a perspective view showing an SIS portion of yet another bioprosthetic device of the present invention being formed to include four tissue layers, similar to FIG. 2, and also showing a synthetic portion of the bioprosthetic device including a first row of multiple fibers positioned to lie between two tissue layers of the SIS portion along a length, L, of the SIS portion and a second row of multiple fibers positioned to lie between two other tissue layers of the SIS portion along a width, W, of the SIS portion;

DETAILED DESCRIPTION OF THE DRAWINGS

Figure 5:
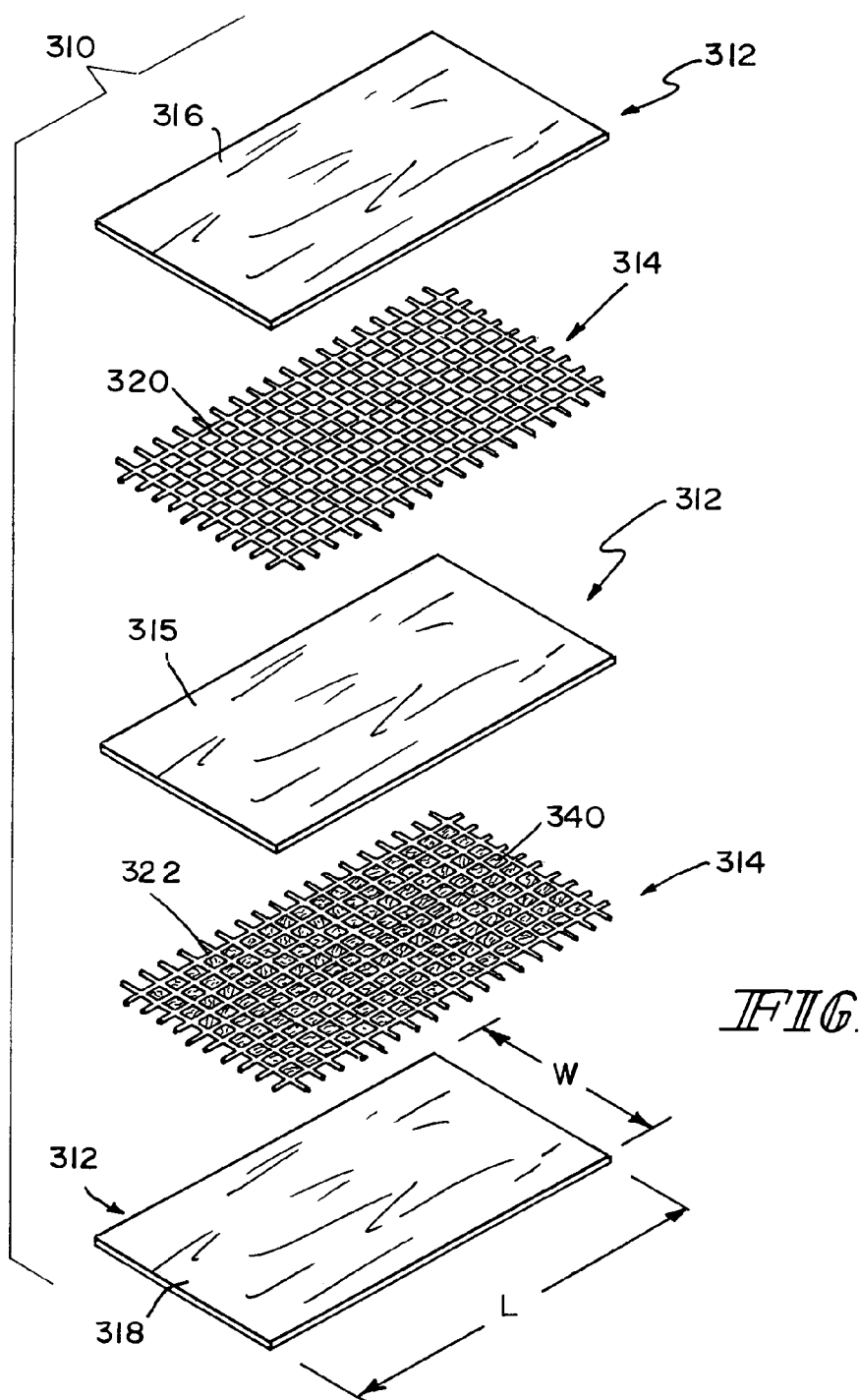
FIG. 5 is an exploded perspective view of another bioprosthetic device of the present invention showing an SIS portion of the prosthetic device including top, bottom, and middle tissue layers and showing a synthetic portion including a first and a second mesh member positioned to lie between the top and middle tissue layers of and the middle and bottom tissue layers of the SIS portion, respectively.

A composite bioprosthetic device 10, as shown in FIG. 1, is provided for the purposes of soft tissue attachment, reinforcement, and/or reconstruction. Bioprosthetic device 10 includes a small intestinal submucosa (SIS) portion 12 and a synthetic portion 14. SIS portion 12 is provided to be absorbed into the body and replaced by host tissue. SIS portion 12 acts as a scaffold for tissue ingrowth and remodeling. Synthetic portion 14 of bioprosthetic device 10 provides additional initial mechanical strength to bioprosthetic device 10. Because device 10 includes SIS portion 12 and synthetic portion 14, bioprosthetic device 10 is provided with a differential in biodegradation and bioremodeling rates. Synthetic portion 14, for example, can be configured to degrade at a slower rate than SIS portion 12. Further, synthetic portion 14 may act as an anchor to couple bioprosthetic device 10 to the surrounding soft tissue (not shown) during surgery.

SIS portion 12 of bioprosthetic device 10, as shown in FIG. 1, includes a top tissue layer 16 and a bottom tissue layer 18 coupled to top tissue layer 16 through a dehydration process. Although top and bottom tissue layers 16, 18 are provided in bioprosthetic device 10 shown in FIG. 1, it is within the scope of this disclosure, as will be described in more detail later, to include SIS portions 12 having any number of tissue layers. It is also included within the scope of this disclosure to provide perforated tissue layers or any other physical configuration of SIS. See FIGS. 2–4, for example. Further, it is within the scope of this disclosure to define top and bottom tissue layers 16, 18 as including multiple tissue layers each. In preferred embodiments, for example, top and bottom tissue layers 16, 18 each include three to four layers of SIS tissue. SIS portion 12 further includes a first end 20, a second end 22 spaced-apart from first end 20, and sides 24 coupled to and positioned to lie between first and second ends 20, 22. A length, L, is defined as the distance between first end 20 and second end 22 and a width, W, is defined as the distance between sides 24.

Synthetic portion 14 of bioprosthetic device 10 includes row 26 of four fibers 28, as shown in FIG. 1. Fibers 28 are positioned to lie along length L between top and bottom tissue layers 16, 18 and are further positioned to lie in coplanar relation to one another. When making bioprosthetic device 10, fibers 28 of synthetic portion 14 are placed between top and bottom tissue layers 16, 18 prior to dehydration. Although row 26 of four fibers 28 is provided in bioprosthetic device 10 shown in FIG. 1, it is within the scope of this disclosure to include synthetic portions 14 formed to include any number of rows 26 having any number of fibers 28. It is further within the scope of this disclosure to include fibers 28 made from bioabsorbable and non-bioabsorbable materials. For example, it is within the scope of this disclosure to include fibers 28 made from polylactic acid (PLA) or polyglycolic (PGA) acid, a combination of the two, Panacryl™ absorbable suture (Ethicon, Inc, Somerville, N.J.), other bioabsorbable materials, nylon, polyethylene, Kevlar™, Dacron™, PTFE, carbon fiber, or other non-bioabsorbable materials.

As shown in FIG. 1, each fiber 28 of bioprosthetic device 10 includes two outer end portions 30 a middle portion 32 coupled to and positioned to lie between outer end portions 30. Middle portion 32 is positioned to lie between top tissue layer 16 and bottom tissue layer 18 of SIS portion 12. Middle portion 32 of fibers 28 helps to provide strength along length, L, of bioprosthetic device 10. One or more outer end portions 30 of fibers 28 can be used for anchoring bioprosthetic device 10 to surrounding soft tissue (not shown). The combination of SIS portion 12 and fibers 28 further provide bioprosthetic device 10 with differential biodegradation rates. For example, fibers 28 of synthetic portion 14 can be made to be non-bioabsorbable or can be made with material that absorbs into the body at a slower rate than SIS portion 12. Uses for bioprosthetic device 10 shown in FIG. 1 include, but are not limited to, ligament or tendon repair.

An alternate bioprosthetic device 110 is shown in FIGS. 2 and 3. Bioprosthetic device 110 include an alternate SIS portion 112 of having top tissue layer 16, bottom tissue layer 18, and two middle tissue layers 115. Top, bottom, and middle tissue layers 16, 18, 115 include one or more layers of SIS tissue each. SIS portion 112, similar to SIS portion 12, also includes a first end 20, a second end 22 spaced-apart from first end 20, and sides 24. Bioprosthetic device 110 further includes an alternate synthetic portion 114 having three rows 26 of four fibers 28. One row 26 is positioned to lie between top tissue layer 16 and one of the middle tissue layers 115. Another row 26 is positioned to lie between the two middle tissue layers 115, and the final row 26 of fibers 28 is positioned to lie between another one of the middle tissue layers 115 and bottom tissue layer 16, as shown in FIG. 3. Fibers 28 of bioprosthetic device 110, similar to fibers 28 of bioprosthetic device 10, are positioned to lie along length, L, of SIS portion 112.

Although fibers 28 of bioprosthetic devices 10, 110 are positioned to lie along length, L, of each respective SIS portion 12, 112, it is within the scope of this disclosure to include a synthetic portion 214 of an alternate bioprosthetic device 210, as shown in FIG. 4, having multi-directional fibers 28 positioned to lie along a length, L, of an SIS portion 212 and along width, W, of SIS portion 212. Synthetic portion 214 of bioprosthetic device 210 includes a first row 226 having seventeen fibers 28 positioned to lie along length, L, of SIS portion 212. Synthetic portion 214 further includes a second row 227 having eighteen fibers 28 positioned to lie along width, W, of SIS portion 212 so that the fibers 28 of first row 226 and second row 227 are positioned to lie orthogonally with respect to each other. Although rows 226 and 227 are positioned to lie in orthogonal relation to one another, it is within the scope of this disclosure to include synthetic portion 214 having first and second rows 226 and 227 that lie at any angular relation to one another. It is also within the scope of this disclosure to include rows 226 and 227 each having any number of fibers 28.

Similar to bioprosthetic device 110 shown in FIG. 2, bioprosthetic device 210 includes a top tissue layer 216, a bottom tissue layer 218, and two middle tissue layers 215, positioned to lie between top and bottom tissue layers 216, 218. As mentioned before, top, bottom, and middle tissue layers 216, 218, 215 are each formed to include one or more layers of SIS tissue. Although SIS portion 212 of bioprosthetic device 210 is shown to include four tissue layers, it is within the scope of the disclosure to include bioprosthetic device 210 having any number of tissue layers. As shown in FIG. 4, first row 226 is positioned to lie between top tissue layer 216 and one of the two middle tissue layers 215 positioned to lie adjacent to top tissue layer 216. Second row 227 is positioned to lie between the other middle tissue layer 215 and bottom tissue layer 218. It is within the scope of this disclosure, however, to include rows 226, 227 positioned to lie between any tissue layer of device 210.

Figure 6:
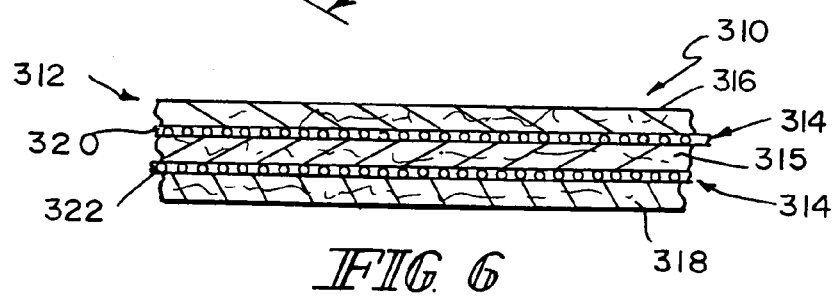
FIG. 6 is a sectional view of the bioprosthetic device of FIG. 5 showing first and second mesh members "sandwiched" between the tissue layers of the SIS portion of the device.

Yet another bioprosthetic device 310 is shown in FIGS. 5 and 6. Bioprosthetic device 310 is similar to devices, 10, 110, and 210 and includes an SIS portion 312 having a top tissue layer 316, a bottom tissue layer 318, and a middle tissue layer 315 positioned to lie between top and bottom tissue layers 316, 318. Top, bottom, and middle tissue layers 316, 318, 315 each include one or more layers of SIS tissue. Bioprosthetic device 310 further includes a synthetic portion 314 including first mesh member 320 and second mesh member 322. It is within the scope of this disclosure to include any type of synthetic mesh member. For example, bioabsorbable and/or non-bioabsorbable mesh members 320, 322 made of either woven or non-woven PGA and/or PLA mixtures are included within the scope of disclosure of this invention. First mesh member 320 is coupled to and positioned to lie between top tissue layer 316 and middle tissue layer 315 and second mesh member 322 is coupled to and positioned to lie between middle tissue layer 315 and bottom tissue layer 318, as shown in FIGS. 5 and 6. As shown, each of the first and second mesh members 320, 322 has a length, L, and a width, W, approximately equal to length, L, and width, W, of tissue layers 315, 316, 318, of SIS portion 312. However, in some embodiments, it may be preferable for the mesh to be slightly smaller.

In FIG. 5, second mesh member 322 is shown partially coated in comminuted SIS 340. Comminuted SIS may be used to fill the interstices of second mesh member 322 to provide a stronger device. Other means for reinforcing bioprosthetic device 10 may be employed, including suturing or tacking the various layers together. Further, while comminuted SIS is discussed with respect to the embodiment shown in FIG. 5, it is understood that comminuted SIS may be used to coat the mesh or fibers for any embodiment.

Figure 7:
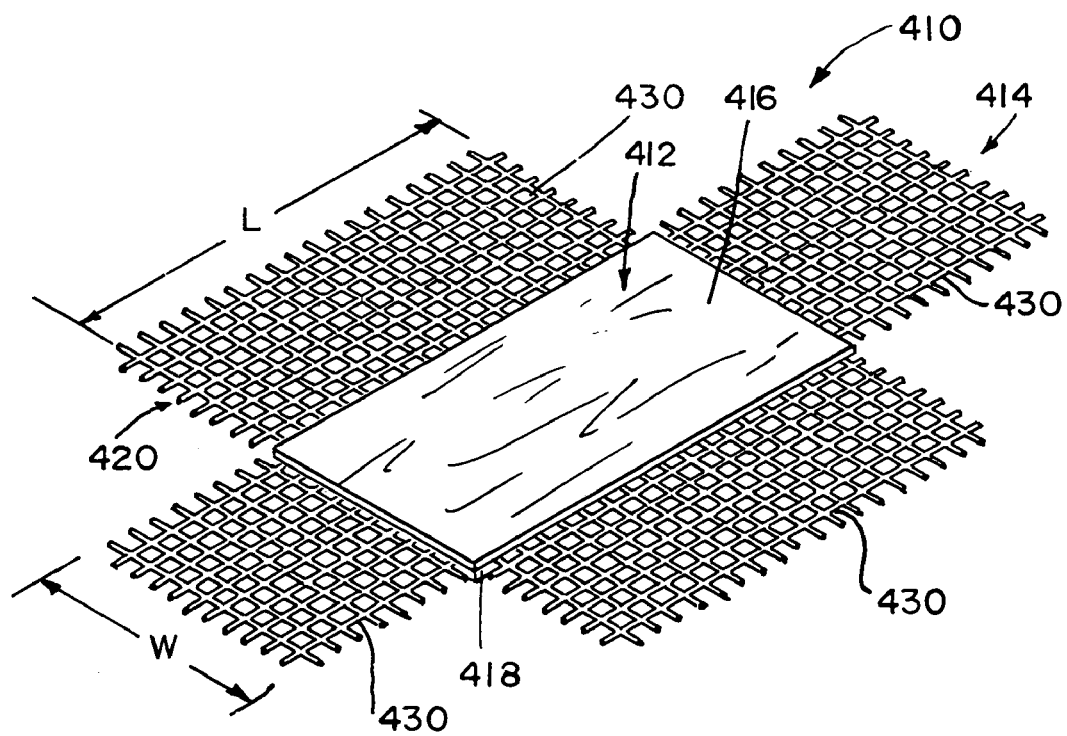
FIG. 7 is a perspective view showing an SIS portion of another bioprosthetic device being formed to include a top and a bottom tissue layer and further showing a synthetic portion being formed to include a mesh member having a body portion positioned to lie between the top and bottom tissue layers and outer wing portions provided for anchoring the device to surrounding soft tissue.

Another embodiment of the present invention includes a bioprosthetic device 410 having a synthetic portion 414 including a mesh member 420, as shown in FIG. 7. Similar to the previously mentioned devices, bioprosthetic device 410 includes an SIS portion 412 having a top tissue layer 416 and a bottom tissue layer 418 coupled to top tissue layer 416. Top and bottom tissue layers 416, 418 each include one or more layers of SIS tissue. Mesh member 420 includes a central body portion (not shown) and outer wing portions 430, as shown in FIG. 7. Outer wing portions 430 are extensions of the central body portion. Although four outer wing portions 430 are shown in FIG. 7, it is within the scope of this disclosure to include a mesh member having a body portion and any number of wing portions 430 coupled to the body portion. The central body portion of mesh member 420 is formed to include a length and a width equal to length, L, and width, W, of SIS portion 412. The central body portion is coupled to and positioned to lie between top tissue layer 416 and bottom tissue layer 418 of SIS portion 420. Each wing portion 430 is coupled to the central body portion of mesh member 420 and is positioned to extend beyond the length, L, and width, W, of SIS portion 412, as shown in FIG. 7. As mentioned before, outer wing portions 430 are extensions of the central body portion. Wing portions 430 provide additional material for anchoring bioprosthetic device 410 to the surrounding soft tissue. Because outer wing portions 430 extend beyond central body portion of mesh member 420, mesh member 420 has a length and a width greater than length, L, and width, W, of SIS portion 412.

Figure 8:
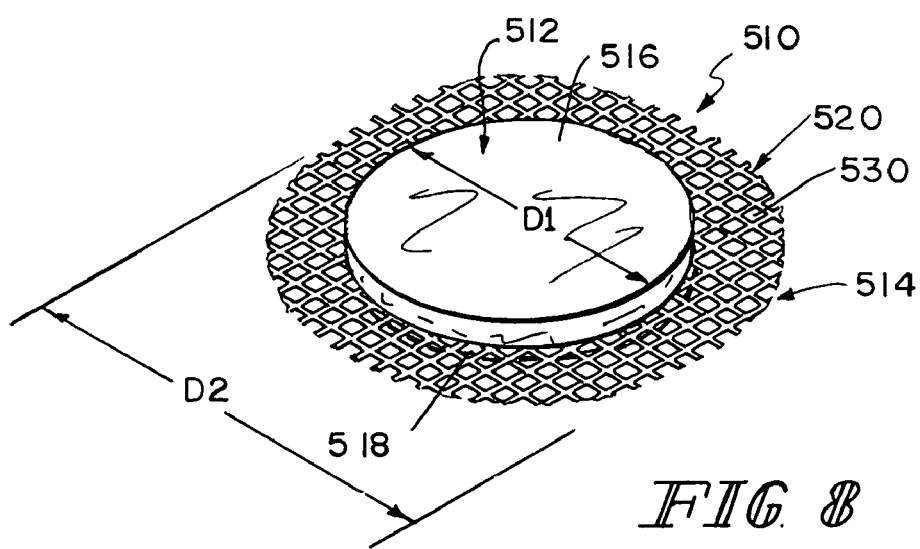
FIG. 8 is a perspective view showing an SIS portion of yet another bioprosthetic device being formed to include a circularly shaped top and bottom tissue layers each having a diameter, D1, and further showing a synthetic portion of the device being formed to include a circular mesh member positioned to lie between the top and bottom tissue layers and having a diameter, D2, which is larger than D1 so that an outer rim portion of the mesh member is formed to extend beyond the top and bottom tissue layers for anchoring the bioprosthetic device to the host tissue during surgery.

Yet another embodiment of the present invention is shown in FIG. 8 showing a bioprosthetic device 510 similar to bioprosthetic device 410, described above. Bioprosthetic device 510 includes an SIS portion 512 and a synthetic portion 514 coupled to SIS portion 512. SIS portion 512 includes a top tissue layer 516 which is circular in shape and a bottom tissue layer 518 which is also circular in shape.

Each of the top and bottom tissue layers 516, 518 include one or more layers of SIS tissue. Top and bottom tissue layers 516, 518 each have a diameter, D1. The synthetic portion 514 of bioprosthetic device 510 includes a mesh member 520 coupled to and positioned to lie between top and bottom tissue layers 516, 518. Mesh member 520 is circular in shape and has a diameter, D2, which is greater than diameter, D1, of synthetic portion 512. Therefore, as shown in FIG. 8, an outer rim portion 530 of mesh member 520 is provided. Similar to outer wing portions 430 of bioprosthetic device 410, shown in FIG. 7, outer rim portion 530 of bioprosthetic device 510 provides additional material for anchoring bioprosthetic device 510 to the surrounding soft tissue during surgery.

Although various embodiments have been described in detail above, it is within the scope of this disclosure to include any bioprosthetic device having an SIS portion and a synthetic portion coupled to the SIS portion in order to provide improved initial mechanical strength of the bioprosthetic device, to obtain desired differential biodegradation and bioremodeling rates, and to provide improved anchoring means of the device to the host tissue. For example, FIGS. 1–8 show the SIS portion including SIS tissue layers in the form of sheets. It is within the scope of this disclosure, however, to further define the SIS portion to include sheets, perforated sheets, or any other physical configuration of SIS. It is also within the scope of this disclosure to include the synthetic portion comprising Prolene™ (Ethicon, Inc, Somerville, N.J.) meshes and/or sutures, Vicryl™ (Ethicon, Inc, Somerville, N.J.) meshes and/or sutures, Mersilene™ (Ethicon, Inc, Somerville, N.J.) meshes, PDS II™ (Ethicon, Inc., Somerville, N.J.) meshes or sutures, Panacryl™ (Ethicon, Inc., Somerville, N.J.) meshes or sutures, and Monocryl™ meshes or sutures, for example. Further it is within the scope of this disclosure to include any bioprosthetic devices where the SIS portion includes any number of tissue layers made from SIS and where multiple tissue layers are positioned to lie between each layer of fibers and/or mesh of the synthetic portion. The SIS layers may be dehydrated prior to or subsequent to assembly of the device.

It is also within the scope of this disclosure to include bioprosthetic device where the synthetic portion is either bioabsorbable or non-bioabsorbable and includes any number of fibers and/or any number of mesh members, as described above. Although FIGS. 1–4 show the synthetic portion being defined by fibers, it is within the scope of the disclosure for the synthetic portion to also be defined by fibers or fibrous materials, for example. Further, any shape and/or orientation of the SIS portion and the synthetic portion of the bioprosthetic device is within the scope of this disclosure; FIGS. 1–8 are merely examples of various embodiments of the present invention.

EXAMPLE 1

Sheets of clean, disinfected porcine SIS material were obtained as described in U.S. Pat. Nos. 4,902,508 and 4,956,178. Ten strips 3.5 inches wide and 6 inches long were cut. The strips were hydrated by placing in RO water, at room temperature, for 5 minutes.

To assemble the implant, five SIS strips were placed on top of each other, while ensuring no air bubbles were trapped between the strips. A knitted Panacryl™ mesh 2 inches wide and 5 inches long, was placed centrally on the 5-layer thick SIS strip. The mesh had been pretreated to remove any traces of oil or other contaminants due to handling. This was done by a series of rinses, each 2 minutes long, in 100%, 90%, 80%, 70% ethanol (200 proof) in RO water, followed by a final 5 minute in RO water. Subsequently, a second 5-layer thick strip of SIS was assembled and placed to sandwich the mesh between the two SIS strips.

The implant was dried under vacuum pressure using a gel drier system (Model FB-GD-45, Fisher Scientific, Pittsburgh, Pa.) for 3 hours. The gel drier bed temperature was set at 30° C. for the procedure. This drying procedure results in "squeezing out" of the bulk water in the implant and also reduces the amount of bound water within the tissue, resulting in a final moisture of between 7%–8%. This process also results in a physical crosslinking between the laminates of SIS and between the mesh and adjacent SIS laminates.

Non-reinforced SIS strips were made in the same way as described, except that no mesh material was placed between the strips of SIS.

EXAMPLE 2

A soaking test was performed to test resistance to delamination. Implants made as specified in Example 1 (both reinforced and non-reinforced) were cut into several strips 1 cm wide by 5 cm long, using a #10 scalpel blade. The strips were immersed in RO water, at room temperature for 1, 2, 5, 10, 20, 30, or 60 minutes. Delamination was detected at the edges of the implants by direct visual observation. All implants showed obvious signs of delamination at 1 hour. In non-reinforced implants, delamination was first visually observed between 40–60 minutes, whereas in the reinforced samples delamination was apparent between 20–30 minutes.

EXAMPLE 3

This example illustrates the enhanced mechanical properties of a construct reinforced with absorbable mesh. Preparation of three-dimensional elastomeric tissue implants with and without a reinforcement in the form of a biodegradable mesh are described. While a foam is used for the elastomeric tissue in this example, it is expected that similar results will be achieved with an ECM and a biodegradable mesh.

A solution of the polymer to be lyophilized to form the foam component was prepared in a four step process. A 95/5 weight ratio solution of 1,4-dioxane/(40/60 PCL/PLA) was made and poured into a flask. The flask was placed in a water bath, stirring at 70° C. for 5 hrs. The solution was filtered using an extraction thimble, extra coarse porosity, type ASTM 170-220 (EC) and stored in flasks.

Reinforcing mesh materials formed of a 90/10 copolymer of polyglycolic/polylactic acid (PGA/PLA) knitted (Code VKM-M) and woven (Code VWM-M), both sold under the tradename VICRYL were rendered flat by ironing, using a compression molder at 80° C./2 min. After preparing the meshes, 0.8-mm shims were placed at each end of a 15.3× 15.3 cm aluminum mold, and the mesh was sized (14.2 mm) to fit the mold. The mesh was then laid into the mold, covering both shims. A clamping block was then placed on the top of the mesh and the shim such that the block was clamped properly to ensure that the mesh had a uniform height in the mold. Another clamping block was then placed at the other end, slightly stretching the mesh to keep it even and flat.

As the polymer solution was added to the mold, the mold was tilted to about a 5 degree angle so that one of the non-clamping sides was higher than the other. Approximately 60 ml of the polymer solution was slowly transferred into the mold, ensuring that the solution was well dispersed in the mold. The mold was then placed on a shelf in a Virtis (Gardiner, N.Y.), Freeze Mobile G freeze dryer. The following freeze drying sequence was used: 1) 20° C. for 15 minutes; 2)–5° C. for 120 minutes; 3)–5° C. for 90 minutes under vacuum 100 milliTorr; 4) 5° C. for 90 minutes under vacuum 100 milliTorr; 5) 20° C. for 90 minutes under vacuum 100 milliTorr. The mold assembly was then removed from the freezer and placed in a nitrogen box overnight. Following the completion of this process the resulting implant was carefully peeled out of the mold in the form of a foam/mesh sheet.

Nonreinforced foams were also fabricated. To obtain non-reinforced foams, however, the steps regarding the insertion of the mesh into the mold were not performed. The lyophilization steps above were followed.

EXAMPLE 4

Lyophilized 40/60 polycaprolactone/polylactic acid, (PCL/PLA) foam, as well as the same foam reinforced with an embedded VICRYL knitted mesh, were fabricated as described in Example 3. These reinforced implants were tested for suture pull-out strength and compared to non-reinforced foam prepared following the procedure of Example 3.

For the suture pull-out strength test, the dimensions of the specimens were approximately 5 cm×9 cm. Specimens were tested for pull-out strength in the wale direction of the mesh (knitting machine axis). A size 0 polypropylene monofilament suture (Code 8834H), sold under the tradename PROLENE (by Ethicon, Inc., Somerville, N.J.) was passed through the mesh 6.25 mm from the edge of the specimens. The ends of the suture were clamped into the upper jaw and the mesh or the reinforced foam was clamped into the lower jaw of an Instron model 4501(Canton, Mass.). The Instron machine, with a 20 lb load cell, was activated using a cross-head speed of 2.54 cm per minute. The ends of the suture were pulled at a constant rate until failure occurred. The peak load (lbs.) experienced during the pulling was recorded.

The results of this test are shown below in Table 1.

TABLE 1

| Suture Pull-Out Data (lbs.) | | | |
| --- | --- | --- | --- |
| Time | Foam | Mesh | Foamed Mesh |
| 0 Day | 0.46 | 5.3 +/– 0.8 | 5.7 +/– 0.3 |
| 7 Day* | — | 4.0 +/– 1.0 | 5.0 +/– 0.5 |

*exposed for 7 days to phosphate buffered saline at 37° C. in a temperature controlled water bath.

These data show that a reinforced foam has improved pull-out strength verses either foam or mesh alone.

Although the invention has been described in detail with reference to certain preferred embodiments, variations and modifications exist within the scope and spirit of the invention as described and defined in the following claims.

The invention claimed is:

1. A bioprosthetic device comprising:
    a sheet of small intestine submucosa; and
    a sheet of bioabsorbable synthetic mesh coupled to the small intestine submucosa, wherein the sheet of synthetic mesh has a rate of absorption that is slower than a rate of absorption of the sheet of small intestine submucosa.

2. The bioprosthetic device of claim 1, wherein the bioprosthetic device is generally planar in shape.

3. The bioprosthetic device of claim 1, wherein the sheet of small intestine submucosa comprises a top tissue layer of small intestine submucosa and is coupled to a bottom tissue layer of small intestine submucosa, and the sheet of synthetic mesh is coupled to and positioned to lie between the top tissue layer and the bottom tissue layer.

4. The bioprosthetic device of claim 3, wherein the sheet of small intestine submucosa is circular in shape and the sheet of synthetic mesh is circular in shape.

5. The bioprosthetic device of claim 1, wherein the sheet of synthetic mesh includes a length and a width equal to or greater than a length and a width of the sheet of small intestine submucosa.

6. The bioprosthetic device of claim 5, wherein the small intestine submucosa is dehydrated and the length and width of the sheet of small intestine submucosa is the same as the length and width of the sheet of synthetic mesh.

7. The bioprosthetic device of claim 1, wherein the sheet of small intestine submucosa comprises multiple layers of small intestine submucosa.

8. The bioprosthetic device of claim 1, wherein the sheet of small intestine submucosa is perforated.

9. The bioprosthetic device of claim 1, wherein the sheet of synthetic mesh is coated with comminuted small intestine submucosa.

10. The bioprosthetic device of claim 1, wherein the synthetic portion comprises a material selected from the group consisting of Prolene™, Vicryl™, and Mersilene™.

11. A bioprosthetic device comprising:
    multiple sheets of naturally occurring extracellular matrix; and
    multiple sheets of synthetic mesh coupled to the naturally occurring extracellular matrix, wherein the bioprosthetic device comprises a stack of the sheets of naturally occurring extracellular matrix separated by the sheets of synthetic mesh.

12. A bioprosthetic comprising:
    a top sheet of small intestinal submucosa comprising multiple small intestine submucosalayers, the top sheet having a first surface area,
    a bottom sheet of small intestine submucosa comprising multiple small intestine submucosa layers, the bottom sheet having a second surface area, wherein the first area and second area are the same;
    and a bioabsorbable mesh device having a third surface area, the mesh device coupled to and positioned to lie between the top and bottom sheets of small intestine submucosa, wherein the sheet of synthetic mesh has a rate of absorption that is slower than a rate of absorption of the sheet of naturally occurring extracellular matrix.

13. The bioprosthetic device of claim 12, wherein the third surface area is equal to the first and second surface areas.

14. The bioprosthetic device of claim 12, wherein the third surface area is greater than the first and second surface areas.

* * * * *